United States Patent [19]

Juneja

[11] 4,302,199

[45] Nov. 24, 1981

[54] HAIR DYEING METHOD

[75] Inventor: Prem S. Juneja, Cincinnati, Ohio

[73] Assignee: The Procter & Gamble Company, Cincinnati, Ohio

[21] Appl. No.: 220,639

[22] Filed: Dec. 29, 1980

[51] Int. Cl.³ .............................................. A61K 7/06
[52] U.S. Cl. ........................................... 8/405; 8/429; 8/594; 8/623; 8/127.51
[58] Field of Search ..................... 8/429, 405, 127.51

[56] References Cited

U.S. PATENT DOCUMENTS

| | | | |
|---|---|---|---|
| 2,313,027 | 3/1943 | Schueller | 8/133 |
| 2,719,104 | 9/1955 | Westerberg | 8/404 |
| 3,128,232 | 4/1964 | Wilmsmann et al. | 8/480 |
| 3,632,295 | 1/1972 | Hall et al. | 8/111 |
| 3,838,966 | 10/1974 | Barchas et al. | 8/405 |
| 3,973,574 | 10/1976 | Minagawa | 8/127.51 |
| 3,973,574 | 8/1976 | Minagawa | 8/127.51 |

OTHER PUBLICATIONS

Venkataraman's "The Chemistry of Synthetic Dyes", vol. V (Academic Press, 1971) pp. 505–507.
Sagarin, E., "Metallic Hair Dyes," Cosmetic Science and Technology, Interscience Publishers, Inc., N.Y., pp. 515–524 (1957).

Primary Examiner—A. Lionel Clingman
Attorney, Agent, or Firm—Douglas C. Mohl; John V. Gorman; Richard C. Witte

[57] ABSTRACT

A method for coloring hair comprising sequentially treating the hair with a solution of water soluble ferric ion salt and with a carboxylic acid solution.

10 Claims, No Drawings

HAIR DYEING METHOD

TECHNICAL FIELD

The present invention involves a novel hair dyeing process wherein the hair is sequentially treated with a solution of a water soluble ferric ion salt and with a carboxylic acid solution.

BACKGROUND ART

The separate use of some of the components involved in the present process is known in the hair dyeing field.

U.S. Pat. No. 3,128,232, Apr. 7, 1964 to Wilmsmann et al discloses dyestuff compositions containing an oxidation dyestuff and 3,4 diaminobenzoic acid or a salt thereof. The acid or salt serves as a toning agent.

U.S. Pat. No. 3,838,966, Oct. 1, 1974 to Barchas et al discloses coloring hair by applying a transition metal to the hair and then oxidizing the metal to form an insoluble oxide. Ferric salts are suitable sources of the transition metal.

Sagarin et al, *Cosmetic Sciences and Technology* (New York, 1957), pp. 515–524, discloses ferric chloride as a modifier for other metal dyes.

While these references disclose compositions which utilize components similar to those utilized in the present process they do not teach or suggest carrying out the process of the present invention.

It is, therefore, an object of the present invention to provide an effective hair dyeing method.

It is a further object of the present invention to provide methods for obtaining a variety of hair colors.

These and other objectives will become readily apparent from the detailed description which follows.

DISCLOSURE OF THE INVENTION

The present invention relates to a method for dyeing hair comprising sequentially applying a solution containing from about 0.01% to about 5% of a water soluble ferric salt and a solution of from about 0.01% to about 10% of a carboxylic acid or water soluble salt thereof.

DETAILED DESCRIPTION OF THE INVENTION

The method of the present invention utilizes a variety of components. Each of these components are discussed in detail below.

Ferric Salt

Various water soluble ferric ion salts are useful in the process of the present invention. Included are the halides, sulfates, nitrates and acetates among many others. Numerous additional salts are listed in any conventional chemical reference text. The preferred salt is ferric chloride.

The ferric salt is applied in the form of a solution, preferably aqueous, and is present at a concentration of from about 0.01% to about 5%, preferably from about 0.5% to about 2%.

Carboxylic Acid

The carboxylic acids useful in the present process include hydroxycinnamic acids and aminobenzoic acids. Typical of such acids are 3,4 dihydroxycinnamic acid, o-hydroxycinnamic acid, p-hydroxycinnamic acid, p-aminobenzoic acid and 3,4-diaminobenzoic acid. The acids can be used in their free state or as water soluble salts such as the alkali metal and ammonium salts.

As with the ferric salt, the carboxylic acid or salt thereof is applied in the form of a solution. The solution is preferably aqueous, has an acid or salt concentration of from about 0.01% to about 10%, preferably of from about 0.5% to about 5% and has a pH of from about 5 to about 10.

Solvent

The preferred solvent for use in the present process is water but other solvents such as ethanol may also be used as cosolvents.

Optional Components

The solutions described above may contain various optional materials such as buffers, surfactants, perfumes among many others. For example, the carboxylic acid may be applied to the hair from a complete shampoo composition.

Method of Manufacture

The solutions of the present process may be made by any of a wide variety of simple mixing techniques.

Usage

The present method as indicated supra involves the sequential applications of the ferric ion salt solution and the carboxylic acid solution. The order of application is not critical although it is preferred to apply the ferric salt solution first.

The type of hair which is most easily treated utilizing the present process is grey/yellow. The movement to blacker shades is obtained with the hydroxycinnamic acids while brown shades are obtained with the aminobenzoic acids. The rate of color change can be controlled by varying the concentration of the active ingredients and/or the number of applications.

The present method may be employed using dry hair or hair that has been previously wetted as in shampooing. In addition the hair may or may not be rinsed between application of the solutions.

The following examples further describe and demonstrate embodiments within the scope of the present invention. The examples are given solely for the purpose of illustration and are not to be construed as limitations of the invention as many variations are possible without departing from its spirit and scope. Unless otherwise indicated, percentages herein are by weight.

EXAMPLE I

A process of the present invention was carried out in the following manner.

A 1% aqueous solution of ferric chloride was prepared.

A second aqueous solution containing 1% 3,4 diaminobenzoic acid was prepared and adjusted to pH6.

A hair swatch containing 2 grams of gray/yellow hair was wetted with water and wiped dry with a paper towel.

The swatch was treated with 1 ml of the ferric chloride solution which was distributed over the entire swatch.

The swatch was then treated with 1 ml of the 3,4 diaminobenzoic acid solution.

One minute after the benzoic acid application the swatch was rinsed with water.

The swatch was subjected to two additional applications of the respective solutions.

When compared with a control, an untreated swatch, the treated swatch had a substantial brown color.

EXAMPLE II

A process of the present invention was carried out in the following manner.

A first aqueous solution containing 1% ferric chloride 5 was prepared.

A second aqueous solution containing 1% 3,4 dihydroxycinnamic acid was prepared and adjusted to pH 8.

A 2 g. swatch of gray/yellow hair was shampooed and treated first with 1 ml of the ferric chloride solution and then with 1 ml of the 3,4 dihydroxycinnamic acid solution.

The swatch was rinsed and dried.

Ten additional cycles of shampoo and treatments were conducted. These were on a morning/afternoon schedule.

When compared with a control, an untreated swatch, the treated swatch had significantly blacker color.

What is claimed is:

1. A method for coloring hair comprising sequentially treating the hair with a solution of from about 0.01% to about 5% of a water soluble ferric ion salt and with a solution of from about 0.01% to about 10% of a carboxylic acid or salt thereof selected from the group consisting of hydroxycinnamic acids, aminobenzoic acids, water soluble salts of these acids and mixtures thereof.

2. A method according to claim 1 wherein the ferric ion salt solution is applied to the hair first.

3. A method according to claim 2 wherein the carboxylic acid is a hydroxycinnamic acid.

4. A method according to claim 3 wherein the carboxylic acid is selected from the group consisting of 3,4 dihydroxycinnamic acid, o-hydroxycinnamic acid, p-hydroxycinnamic acid, water soluble salts of these acids, and mixtures thereof.

5. A method according to claim 4 wherein the ferric ion salt is ferric chloride.

6. A method according to claim 5 wherein the hair is wetted prior to the ferric chloride treatment.

7. A method according to claim 2 wherein the carboxylic acid is an aminobenzoic acid.

8. A method according to claim 7 wherein the carboxylic acid is selected from the group consisting of p-aminobenzoic acid, 3,4-diaminobenzoic acid, water soluble salts of these acids and mixtures thereof.

9. A method according to claim 8 wherein the ferric ion salt is ferric chloride.

10. A method according to claim 9 wherein the hair is wetted prior to the ferric chloride treatment.

* * * * *